(12) United States Patent
Lam (10) Patent No.: US 6,468,541 B2
(45) Date of Patent: Oct. 22, 2002

(54) NATURAL, NON-ALLERGENIC, IMMUNE SYSTEM STIMULANT

(75) Inventor: Paul Y. S. Lam, Los Angeles, CA (US)

(73) Assignee: Chinese Herbal USA, Inc., Los Angeles, CA (US)

( * ) Notice: Subject to any disclaimer, the term of this patent is extended or adjusted under 35 U.S.C. 154(b) by 0 days.

(21) Appl. No.: 09/885,089

(22) Filed: Jun. 21, 2001

(65) Prior Publication Data

US 2002/0044947 A1 Apr. 18, 2002

Related U.S. Application Data (63) Continuation-in-part of application No. PCT/US00/24428, filed on Aug. 31, 2000.
(60) Provisional application No. 60/279,457, filed on Mar. 29, 2001.

(51) Int. Cl.[7] .................... A61K 35/78; A61K 9/14; A61K 35/84; A61P 37/04
(52) U.S. Cl. .................... 424/195.1; 514/885; 514/783; 424/451; 424/464; 424/489
(58) Field of Search ................... 514/885, 783; 424/451, 456, 464, 489, 195.1

(56) References Cited

FOREIGN PATENT DOCUMENTS

| CN | 1102113 A | * | 5/1995 |
| CN | 1133189 A | * | 10/1996 |
| CN | 1147917 A | * | 4/1997 |

OTHER PUBLICATIONS

Chevallier, A. The Encyclopedia of Medicinal Plants. 1996. DK. pp. 65, 99, 200 and 215.*

Gennaro et al. Remington's Pharmaceutical Sciences. 1990. Mack. Ed. 18th. pp. 1294–1295.*

Mao et al., "Effects of a Combination of Traditional Chinese Botanicals (Immune°) on the Secretion of Interleukin–1β and Interferon–γ by Peripheral Blood Polynuclear Cells," (J. Med. Food 4(1):1–7 (2001).

Arase, Y., Ikeda, K., Murashima, N., Chayama, K., Tsubota, A., Koida, I., Suzuki, Y., Saitoh, S., Kobayashi, M. and Kumada, H. (1997). The long term efficacy of glycyrrhizin in chronic hepatitis C patients. Cancer 79, 1494–1500.

Boehm, U., Klamp, T., Groot, M. and Howard, J. (1997). Cellular responses to interferon–g. Annu Rev Immunol 15, 749–795.

Cassidy, C.M. (1998). Chinese medicine users in the United States part I: utilization, satisfaction, medical plurality. J. Alt. Comp. Med. 4, 17–27.

Cassidy, C.M. (1998). Chinese medicine users in the United States part II: preferred aspects of care. J. Alt. Comp. Med. 4, 189–202.

Choate, C.J., "Modern Medicine and Traditional Chinese Medicine," J. Chinese Med. 60, 27–36 (1999).

Chu, D.T., Lepe–Zuniga, J., Wong, W.L., LaPushin, R. and Mavligit, G.M. (1988). Fractionated extract of *Astragalus membranaceus*, a Chinese medicinal herb, potentiates LAK cell cytotoxicity generated by a low dose of recombinant interleukin–2. J Clin Lab Immunol 26, 183–187.

(List continued on next page.)

Primary Examiner—Edward J. Webman
Assistant Examiner—Helen Nguyen
(74) Attorney, Agent, or Firm—Jeffrey I. Auerbach; Liniak, Berenato, Longacre & White, LLC (57) ABSTRACT

The invention concerns an immune system stimulator comprising Hericium, Radix Astragali, *Cordyceps Sinensus*, Radix Glycyrrhizae and *Dioscoreae Oppositae*. The composition is capable of mediating enhanced production of Interleukin-1 beta without causing an increase in the production of Interleukin-4.

25 Claims, 3 Drawing Sheets

OTHER PUBLICATIONS

Chu, D.T., Wong, W.L. and Mavligit, G.M. (1988). Immunotherapy with Chinese medicinal herbs. II. Reversal of cyclophosphamide–induced immune suppression by administration of fractionated *Astragalus membranaceus* in vivo. J Clin Lab Immunol 25, 125–129.

Eisenberg, D.M., Davis, R.B., Ettner, S.L., Appel, S., Wilkey, S., Van Rompay, M. and Kessler, R.C. (1998). Trends in alternative medicine use in the United States, 1990–1997: results of a follow–up national survey. JAMA, J. Am. Med. Assoc. 280, 1569–1575.

Eisenberg, D.M., Kessler, R.C., Foster, C., Norlock, F.E., Calkins, D.R. and Delbanco, T.L. (1993). Unconventional medicine in the United States: prevalence, costs, and patterns of use. N. Engl. J. Med. 328, 246–252.

Jin, R. and Kurashige, S. (1996). Effects of Chinese herbs on macrophage functions in N–butyl–N–butanolnitrosoamine treated mice. Immunopharmacol Immunotoxical 18, 105–114.

Jiezhong, X., "Senile Dimentia Experience in Treatment According to Differentiation of Patterns," J. Chinese Med. 53, 9–13 (1997).

Kobayashi, M., Herndon, D.N., Pollard, R.B. and Suzuki, F. (1995). CD4+ contrasuppressor T cells improve the resistance of thermally injured mice infected with HSV. J Leukoc Biol 58, 159–167.

Kobayashi, M., Schmitt, D.A., Utsunomiya, T., Pollard, R.B. and Suzuki, F. (1993). Inhibition of burn–associated suppressor cell generation by glycyrrhizin through the induction of contrasuppressor T cells. Immunol Cell Biol 71, 181–189.

Kuo, Y.C., Tsai, W.J., Shiao, M.S., Chen, C.F. and Lin, C.Y. (1996). Cordyceps sinensis as an immunomodulatory agent. Am J Chin Med 24, 111–125.

Kurashige, S., Akuzawa, Y. and Endo, F. (1999). Effects of astragali radix extract on carcinogenesis, cytokine production, and cytotoxicity in mice treated with a carcinogen, N–butyl–N'–butanolnitrosoamine. Cancer Invest 17, 30–35.

Lu et al., "Effect of Zi Gui Decoction on Immune Function in 60Co gamma–irradiated mice," Zhonghua Fangshe Yixue Yu Fanghu Zazhi, 1995 15(i) pp. 17–19.

Lin CY et al., "Inhibition of activated human mesangial cell proliferation by the natural product of Cordyceps sinensis (H1–A): an implication for treatment of IgA mesangial nephropathy," J Lab Clin Med 1999 Jan;133(1):55–63.

MacLennan, A.H., Wilson, D.H. and Taylor, A.W. (1996). Prevalence and cost of alternative medicine in Australia. Lancet 347, 569–573.

Matsumoto, T., Tanaka, M., Yamada, H. and Cyong, J.–C. (1996). Effect of licorice roots on carrageenan–induced decrease in immune complexes clearance in mice. J Ethnopharmacol 53, 1–4.

Matsuura K, Kawakita T, Nakai S, Saito Y, Suzuki A and Nomoto K. (1993). Role of B–lymphocytes in the immunopharmacological effects of a traditional Chinese medicine, Xiao–Chai–Hu–Tang (Shosaiko–to). Int. J. Immunopharmacol. 15, 237–243.

Mikamo, H., Kawazoe, K., Sato, Y., Hayasaki, Y., Izumi, K. and Tamaya, T. (1999). Effects of crude herbal ingredients on serum levels of inflammatory cytokines in a rat uterine endometritis model. Curr Ther Res 60, 105–110.

Mizuno T. (1995). Yamagushitake, Hericium erinaceum: Bioactive substances and medicinal utilization. Food Rev Int 11, 173–178.

Nakajima, N., Utsunomiya, T., Kobayashi, M., Herndon, D.N., Pollard, R.B. and Suzuki, F. (1996). In vitro induction of anti–type 2 T cells by glycyrrhizin. Burns 22, 612–617.

Nakamura, K., Yamaguchi, Y., Kagota, S., Shinozuka, K. and Kunitomo, M. (1999). Activation of in vivo Kupffer cell function by oral administration of Cordyceps sinensis in rats. Jpn J Pharmacol 79, 505–508.

Rittenhouse, J.R., Lui, P.D. and Lau, B.H.S. (1991). Chinese medicinal herbs reverse macrophage suppression induced by urological tumors. J Urol 146, 486–490.

Shinada, M., Azuma, M., Kawai, H., Sazaki, K., Yoshida, T., Suzutani, T. and Sakuma, T. (1986). Enhancement of interferon–gamma production in glycyrrhizin–treated human peripheral lymphocytes in response to concanavalin A and to surface antigen of hepatitis B virus. Proc Soc Exp Biol Med 181, 205–210.

Song, Q.–H., Kobayashi, T., Xiu, L.–M., Hong, T. and Cyong, J.–C. (2000). Effects of Astragali root and Hedysari root on the murine B and T cell differentiation. J Ethnopharmacol 73, 111–119.

Sun, Y., Hersh, E.M., Talpaz, M., Lee, S., Wong. W., Loo, T.L. and Mavligit, G.M. (1983). Immune restoration and/or augmentation of local graft versus host reaction by traditional Chinese medicinal herbs. Cancer Invest 52, 70–73.

Tomlinson, B., Chan, T.Y.K., Chan, J.C.N., Critchley, J.A.J.H. and But, P.P.H. (2000). Toxicity of complementary therapies: An eastern perspective. Journal of Clinical Pharmacology 40, 451–456.

Utsunomiya, T., Ito, M., Pollard, R.B. and Suzuki, F. (2000). Glycyrrhizin improves the resistance of MAIDS mice to opportunistic infection of *Candida albicans* through the modulation of MAIDS–associated type 2 T cell responses. Clin Immunol 95, 145–155.

Utsunomiya, T., Kobayashi, M., Herndon, D.N., Pollard, R.B. and Suzuki, F. (1995). Glycyrrhizin (20b–carboxy–11–oxo–30–norolean–12–en–3 b–yl–2–O–b–D–glucopyranuronosyl–a–D glucopyranosiduronic acid) improves the resistance of thermally injured mice to opportunistic infection of herpes simplex virus type 1. Immuno Lett 44, 59–66.

Utsunomiya, T., Kobayashi, M., Herndon, D.N., Pollard, R.B. and Suzuki, F. (1998). Recovery of impaired IL–12 production in thermally injured mice treated with glycyrrhizin (GR), and active component of licorice roots. FASEB J 12, A271.

Utsunomiya, T., Kobayashi, M. Herndon, D.N., Pollard, R.B. and Suzuki, F. (1999). Effects of glycyrrhizin, an active component of licorie roots, on *Candida albicans* infection in thermally injured mice. Clin Exp Immunol 116, 291–298.

Utsunomiya, T., Kobayashi, M., Pollard, R.B. and Suzuki, F. (1999). Restoration of the impaired production of IL–12 in MAIDS mice treated with glycyrrhizin. Am Soc Microbiol Abstr General Meeting 99, 289.

van Rossum, T., Vulto, A., de Man, R., Brouwer, J. and Schalm, S. (1998). Review article: glycyrrhizin as a potential treatment for chronic hepatitis C. Aliment Pharmacol Ther 12, 199–205.

Xu HM, Xie ZH, Zhang WY, "Immunomodulatory function of polysaccharide of Hericium erinaceus". Zhongguo Zhong Xi Yi Jie He Za Zhi 1994 Jul; 14(7):427–8.

Xu, R.H., Peng, X.E., Chen, G.Z. and Chen, G.L. (1992). Effects of cordyceps sinensis on natural killer activity and colony formation of B16 melanoma. Chin Med J (Engl). 105, 97–101.

Yamada H, Kiyohara H, Takemoto N, Zhao J–F, Kawamura H, Komatsu Y, Cyong J–C, Aburada M and Hosoya E. (1992). Mitogenic and complement activating activities of the herbal components of Juzen–taiho–to. Planta Med. 58, 166–170.

Yamashiki, M., Nishimura, A., Suzuki, H., Sakaguchi, S. and Kosaka, Y. (1997). Effects of the Japanese herbal medicine "Sho–saiko–to" (TJ–9) on in vitro interleukin–10 production by peripheral blood mononuclear cells of patients with chronic hepatitis C. Hepatology 25, 1390–1397.

Yoshida, Y., Wang, M.Q., Liu, J.N., Shan, B.E. and Yamashita, U. (1997). Immunomodulating activity of Chinese medicinal herbs and *Oldenlandia diffusa* in particular. Int J Immunopharmacol 19, 359–370.

Zhang, Y.H., Isobe, K., Nagase, F., Lwin, T., Kato, M., Hamaguchi, M. and Yokochi, T. (1993). Glycyrrhizin as a promoter of the late signal transduction for interleukin–2 production by splenic lymphocytes. Immunology 79, 528–534.

Zhao, K.S., Mancini, C. and Doria, G. (1990). Enhancement of the immune response in mice by *Astragalus membranaceus* extracts. Immunopharmacology 20, 225–233.

Zhu, J.–S., Halpern, G.M. and Jones, K. (1998). The scientific rediscovery of an ancient Chinese herbal medicine: Cordyceps sinensis. Part I. J Altern Complement Med 4, 289–303.

Zhu, J.–S., Halpern, G.M. and Jones, K. (1998). The scientific rediscovery of an ancient Chinese herbal medicine: Cordyceps sinesis. Part II. J Altern Complement Med 4, 429–457.

* cited by examiner

NATURAL, NON-ALLERGENIC, IMMUNE SYSTEM STIMULANT

CROSS-REFERENCE TO RELATED APPLICATION

This application is a continuation-in part of U.S. patent application Ser. No. 60/279,457, filed Mar. 29, 2001, which is a continuation-in part of PCT Application Serial No. PCT/US00/24428, filed on Aug. 31, 2000, herein incorporated by reference.

FIELD OF THE INVENTION

This invention relates to dietary supplements. More particularly, this invention relates to supplements which will stimulate the immune system without producing an allergic response.

BACKGROUND OF THE INVENTION

Recently, evidence has been accumulating that herbal supplements, taken regularly, may have beneficial effects. Herbal supplements, unlike medicines, are not effective instantaneously but must be taken over long periods of time in order to be effective. In other words, it takes time to create an effect in humans. There are many products on the market that claim to stimulate the immune system but the research behind such products seems to be borderline at best. See article on functional food to be published in California agriculture 2000, probably in November 2000 issue. Stimulating the immune system is a perfect application for herbal supplements because the immune system can be improved gradually. An improved immune system can be beneficial in fighting all kinds of illnesses from the common cold to deadly cancers.

Unfortunately, many herbal supplements can create an allergic response in humans. What is needed is a dietary supplement or herbal supplements that can stimulate the human immune system without inducing an allergic response. It is also important that this product have been properly tested for efficacy. Development of an herbal supplement that can stimulate the immune system without producing an allergic response presents a great improvement in the field of medicine and satisfies a long felt need of medical practitioners and of their patients.

SUMMARY OF THE INVENTION

In detail, the invention concerns an immune system stimulator compositions comprising Hericium, Radix Astragali, Cordyceps Sinensus, Radix Glycyrrhizae and Dioscoreae Oppositae. The invention particularly concerns such immune system stimulator compositions wherein the compositions comprise 5–80% by weight Hericium, 5–40% by weight Radix Astragali, 5–40% by weight Cordyceps Sinensus, 1–40% by weight Radix Glycyrrhizae and 5–40% by weight Dioscoreae Oppositae, and more particularly, The immune system stimulator of claim 1, wherein said stimulator comprises 40–70% by weight Hericium, 10–50% by weight Radix Astragali, 5–30% by weight Cordyceps Sinensus, 1–30% by weight Radix Glycyrrhizae and 5–30% by weight Dioscoreae Oppositae.

The invention is particularly concerned with embodiments of such compositions, wherein all ingredients are powdered, and/or wherein a biologically effective amount of the ingredients are present in a biologically effective amount per dose (preferably containing 100 mg total amount per dose).

The invention is particularly concerned with embodiments of the above compositions in which a biologically effective amount of the ingredients are incorporated into a pill, a capsule, or a gel cap (preferably containing 100 mg total amount per dose).

The invention additionally concerns a method of making an immune system stimulator comprising the steps of:

(a) obtaining powdered Hericium, Radix Astragali, Cordyceps Sinensus, Radix Glycyrrhizae, and Dioscoreae Oppositae; and (b) mixing 5–80% by weight Hericium, 5–40% by weight Radix Astragali, 5–40% by weight Cordyceps Sinensus, 1–40% by weight Radix Glycyrrhizae and 5–40% by weight Dioscoreae Oppositae together.

The invention is particularly concerned with embodiments of the above methods wherein method further comprises formulating biologically effective amounts of the ingredients of the mixture into a pill, a capsule, or a gel cap (preferably containing 100 mg total amount per dose).

The invention further provides a method of stimulating the immune system of a human or other mammal comprising providing to the human or other mammal a biologically effective amount of an immune system stimulator comprising Hericium, Radix Astragali, Cordyceps Sinensus, Radix Glycyrrhizae and Dioscoreae Oppositae. The invention particularly concerns the embodiment of such method wherein the stimulator comprises a biologically effective amount of an immune system stimulator comprising 5–80% by weight Hericium, 5–40% by weight Radix Astragali, 5–40% by weight Cordyceps Sinensus, 1–40% by weight Radix Glycyrrhizae and 5–40% by weight Dioscoreae Oppositae, and more particularly, wherein the stimulator comprises 40–70% by weight Hericium, 10–50% by weight Radix Astragali, 5–30% by weight Cordyceps Sinensus, 1–30% by weight Radix Glycyrrhizae and 5–30% by weight Dioscoreae Oppositae. The invention particularly concerns the embodiment of such method wherein the biologically effective dose comprises 100 mg.

DESCRIPTION OF THE PREFERRED EMBODIMENTS

The present invention comprises a mixture of five natural herbs: Hericium, Radix Astragali, Cordyceps Sinensus, Radix Glycyrrhizae and Dioscoreae Oppositae. In a preferred embodiment, the composition will be formulated to comprise 5–80% by weight Hericium, 5–40% by weight Radix Astragali, 5–40% by weight Cordyceps Sinensus, 1–40% by weight Radix Glycyrrhizae and 5–40% by weight *Dioscoreae Oppositae*. Preferably, the powders are size 80 (i.e., the powders were passed through a sieve with 80 holes. This is a Chinese standard used in measuring herbal powder).

The mixture can be administered in any acceptable form such as in capsules, pressed into tablets, and made into gel caps. Gel caps are recent development in which a powder is placed in suspension in a fluid and then ease and calculated with a gel. The preferred dosage is 100 mg of the composition of the present invention, twice a day (for example, 100 mg at breakfast and 100 mg before bed).

This invention was tested by the following procedure at the Department Of Clinical Immunology at the University of California at Davis, Calif.:

1. Collect blood;
2. Isolate white blood cells;
3. Isolate lymphocytes;
4. Incubate leukocytes in mini tubes for varying periods of time in the presence or absence of the composition of the present invention;
5. Incubate the lymphocytes with four serial ten-fold dilutions of the composition of the present invention from 0.1 to 100 µg/ml;
6. Repeat the same experiments in the presence or absence of phytohemagglutinin (PHA), a known as stimulator of cells;
7. Collect the culture supernatants (i.e., the fluid above the lymphocytes);
8. Using known standards and a reference curve, assay the supernatants for Interleukin 1 (IL-1) beta and Interleukin 4 (IL-4);

The results showed an impressive production of IL-1 beta without an increase in IL-4. Such production would be helpful during periods of needed immune response, i.e., during a cold or infection.

BEST MODE FOR CARRYING OUT INVENTION

This invention comprises the following mixture. All ingredients are naturally occurring herbs. In a preferred embodiment, the composition will comprise Hericium at a concentration of 5–80%; Radix Astragali at a concentration of 5–80%; *Cordyceps Sinensus* at a concentration of 5–80%; Radix Glycyrrhizae at a concentration of 1–40%; and *Dioscoreae Oppositae* at a concentration of 5–80%. In a more preferred embodiment, the composition will comprise Hericium at a concentration of 40–70%; Radix Astragali at a concentration of 10–50%; *Cordyceps Sinensus* at a concentration of 5–30%; Radix Glycyrrhizae at a concentration of 1–30%; and *Dioscoreae Oppositae* at a concentration of 5–30%. In the most preferred embodiment, the composition will comprise Immune+™ distributed by Zen-Tech, Inc. (Los Angeles, Calif.).

Having now generally described the invention, the same will be more readily understood through reference to the following examples, which are provided by way of illustration, and are not intended to be limiting of the present invention, unless specified.

EXAMPLES

Example 1

In Vitro Analysis of Herbal Product

Treatment preparation. 10 mg of herbal product was suspended in 1 ml of RPMI-1640 culture medium supplemented with 10% heat inactivated fetal bovine serum (media). The suspension was shaken vigorously on a vortex mixer. The insoluble components were quickly pelleted and the remaining suspension filtered twice: first through a 0.45 micron syringe filter, and then through a 0.2 micron syringe filter. This filtrate was used as the stock solution (approximately 10 mg/ml) from which dilutions were made for the incubations with peripheral blood mononuclear cells (PBMC). The stock solution was diluted in media prior to treatment with PBMC.

PMBC Isolation. Peripheral blood from six healthy volunteers was collected and the PBMC isolated over a density gradient via centrifugation. The cells were re-suspended in RPMI-1640 medium containing 10% fetal bovine serum and supplemented with 0.1% of a 50 mg/ml gentamicin solution (Gibco BRL, Grand Island Nebr). PBMC concentration was adjusted to $2\times10^6$ viable cells/ml after estimation of viability by trypan blue exclusion assay. Viability was consistently greater than 96%.

Culture of PBMC with Herbal Products. Five hundred ml of a $1.0\times10^6$ cell suspension were cultured with equal volume of the product treatments at 37° C. with 5% carbon dioxide in 48-well plates. PBMCs were exposed to a final concentration of 100, 10, 1, or 0.1 mg/ml of product. In addition, each product treatment was incubated in the presence of PHA at 10 mg/ml. Culture supernatants fractions were harvested after 72 hours and were stored at −20° C. until analysis by enzyme linked immunoassay (ELISA).

ELISA Analysis of Cytokines. Levels of IL-1, IL-4 and gamma interferon (IFN) were measured in supernatants from $1.0\times10^6$ cells/ml stimulated with product in the presence or absence of PHA. For quantitation of secretory IL-4, a high sensitivity Quantikine Human IL-4 ELISA kit was used with the detection limit of 0.25 pg/ml (R&D systems, Minneapolis, Minn.). Standard ELISA kits were used to quantitate IL-1 and IFN (R&D systems, Minneapolis, Minn.) with detection limits of 3.9 and 31.2 pg/ml respectively.

Results showed an increase of IL-1 beta of between 6 and 11 times without any increase in IL-4. In other words, this product stimulated the human immune system without stimulating IL-4, a precursor to allergies in the human body. This testing was conducted by M. Eric Gershwin, M.D., The Jack and Donald Chia Professor of Medicine, Chief, Division of Rheumatology, Allergy, and Clinical Immunology, University of California, Davis.

Example 2

Investigation of the Effects of a Combination of Traditional Chinese Botanicals (Immune+™) on the Secretion of Interleukin-1β and Interferon-β by Peripheral Blood Mononuclear Cells The use of herbal and other botanical products, including those used extensively in traditional Chinese medicine (TCM), has increased dramatically in the last decade. Yet, little scientific research exists concerning their efficacy and safety. The effects of Immune+™, a combination of five botanicals frequently used in traditional Chinese medicine, on the production of two cytokines was examined. For this purpose, unstimulated or phytohemagglutinin (PHA)-stimulated peripheral blood mononuclear cells (PBMC) from healthy volunteers were incubated with different concentrations of Immune+™. The secretion of interleukin (IL)-1β and interferon (IFN)-γ was measured after 72 h of incubation. At the highest concentration tested (100 µg/ml), Immune+™ significantly increased the secretion of IL-1β. Importantly, PHA alone had no effect on IL-1β production, and the combination of PHA with Immune+™ resulted in the same increase in IL-1β production as seen with the botanical extract alone. Immune+™ did not have any detectable effect on either unstimulated or PHA-stimulated IFN-γ synthesis. These in vitro data support the concept that Immune+™ may enhance human immune responses.

Herbal and other botanical products, along with other forms of complementary and alternative medicine (CAM), have become increasingly popular in the United States and other western countries (Eisenberg et al., 1998, Eisenberg et al., 1993, MacLennan et al., 1996). Traditional Chinese medicine (TCM) has a particularly long-standing and elaborate tradition of making medicinal botanicals an integral part of therapy. A recent survey indicates that there is growing interest in TCM, including herbal preparations, in the United States and that non-Asian populations constitute the largest user group (Cassidy, 1998, Cassidy, 1998).

In TCM, the use of a single plant extract is uncommon. Instead, between four and twelve plants are combined in specific proportions. It is thought that such combinations provide greater benefits because individual components enhance the activities and/or inhibit or reduce the toxicities of the other components (Tomlinson et al., 2000). Mixtures of several plant extracts have, indeed, been shown to exert different—stronger, weaker, or even opposite—effects than individual plant extracts (Matsuura K et al., 1993, Yamada H et al., 1992). However, it remains to be established which of these different effects are desirable in the conditions for which these botanical combinations are most frequently used.

In the present study, the combined effects of five herbal ingredients: Radix Glycyrrhizae (*Glycyrrhiza uralensis* Fisch., *G. inflata*, and *G. glabra*), Radix Astragali (*Astragalus membranaceus* (Fisch.) and *Astragalus mongholicus* [*Astragalus membranaceus* Bge. var. *mongholicus*]), *Dioscoreae rhizoma* (*Dioscorea opposita*), *Cordyceps sinensis* (Berk.) Sacc., and *Hericium erinaceum*, was investigated. To do this, the product Immune+™ (distributed by Zen Tech, Inc., Los Angeles, Calif.), which contains these five ingredients was employed.

Although the five ingredients being tested are frequently found in TCM, their combined formulation (as in Immune+™) is not one of the standard formulae of TCM. Therefore, no research has previously been conducted on this particular combination of botanicals, although data are available on most of the individual ingredients.

Interferon-γ is important in determining the differentiation of CD4 T cells into Th1 rather than Th2 T cells (Boehm et al., 1997) and thereby exerts a vital influence on the host response not only to viral and bacterial infections but also to tumors. Several of the ingredients of Immune+™ have been reported to influence the production of IFN-γ, and almost all are used in the treatment of cancer patients. Therefore, the effect of Immune+™ on the in vitro synthesis of this cytokine by unstimulated and stimulated PBMC from healthy volunteers was investigated. The existing data also indicates that ingredients of Immune+™ stimulate the non-adaptive arm of the immune system, particularly macrophages. IL-1β is not only produced by activated macrophages but further stimulates them. Yet, little data exists on the effects of any of the ingredients of Immune+™ on the production of this cytokine. The effect of Immune+™ on IL-1 β synthesis by unstimulated and stimulated PBMC was therefore examined.

Materials and Methods

Stock solution

Ten mg of Immune+™ was suspended in 1 ml RPMI-1640 with 10% heat inactivated fetal bovine serum (media). The suspension was shaken vigorously on a vortex mixer. The insoluble components were quickly pelleted and the remaining suspension filtered twice: first through a 0.45 micron syringe filter followed by a 0.2 micron syringe filter. This filtrate was used as our stock (approx. 10 mg/ml) from which dilutions were made for the incubations with PBMC. The stock solution was diluted in media prior to treatment with PBMC.

Peripheral blood mononuclear cell (PBMC) isolation

Volunteers of various ethnic backgrounds and ranging in age from 18–35 years, participated in this study. Peripheral blood was collected into sodium citrate-containing tubes and mixed 1:1 with Hanks' Balanced Salt Solution (HBSS; Gibco BRL, Gaithersburg, Md.) without calcium chloride, magnesium chloride, or magnesium sulfate. The diluted blood was then layered over an Accu-Paque gradient (Accurate Chemical and Scientific Corp., Westbury, N.Y.) and centrifuged at 500 g for 30 minutes at room temperature. PBMC were harvested from the interface layer, washed twice with HBSS. The cells were resuspended in RPMI 1640 (Gibco BRL) containing 10% fetal bovine serum and supplemented with 0.1% of a 50 mg/ml gentamicin solution (Gibco BRL). The PBMC concentration was adjusted to $2 \times 10^6$ viable cells per milliliter. Viability was determined by trypan blue exclusion and was consistently >96%. All data was verified by at least three separate experiments.

Culture of PBMC with Immune+™

Five hundred microliters of this $2.0 \times 10^6$ cell suspension, i.e., $1.0 \times 10^6$ cells, were cultured in 48-well plates with an equal volume of each of the four concentrations of Immune+™ in the presence or absence of phytohemagglutinin (PHA) at a final concentration of 10 μg/ml. All treatments were performed in duplicate. After incubation at 37° C. in 5% $CO_2$ for 72 h, the supernatant fractions were harvested for enzyme-linked immunosorbent assay (ELISA) analysis.

ELISA analysis of L-1 β and IFN-γ

Aliquots of culture supernates were frozen immediately upon harvest and stored at −20° C. until analysis by ELISA. Concentrations of IL-1 β and IFN-γ were determined using the DuoSet® ELISA Development System (R & D Systems, Minneapolis, Minn.) with a detection limit of 3.9 and 15.6 pg/ml respectively.

Statistics

The effects of various concentrations of Immune+™ on IL-1β and IFN-γ production in either unstimulated or PHA-stimulated PBMC were analyzed using a one-way ANOVA followed by post-hoc Tukey comparison. The results are presented as means±standard error of the mean (SEM). Results were considered statistically significant when $p < 0.001$.

Results

PBMC from healthy volunteers were incubated for 72 h with either media alone (control), four different concentrations of Immune+™, or the same concentrations of Immune+™ together with 10 μg/ml of PHA. The concentrations of IL-1β and IFN-γ in the supernate were measured by ELISA.

Figure 1:
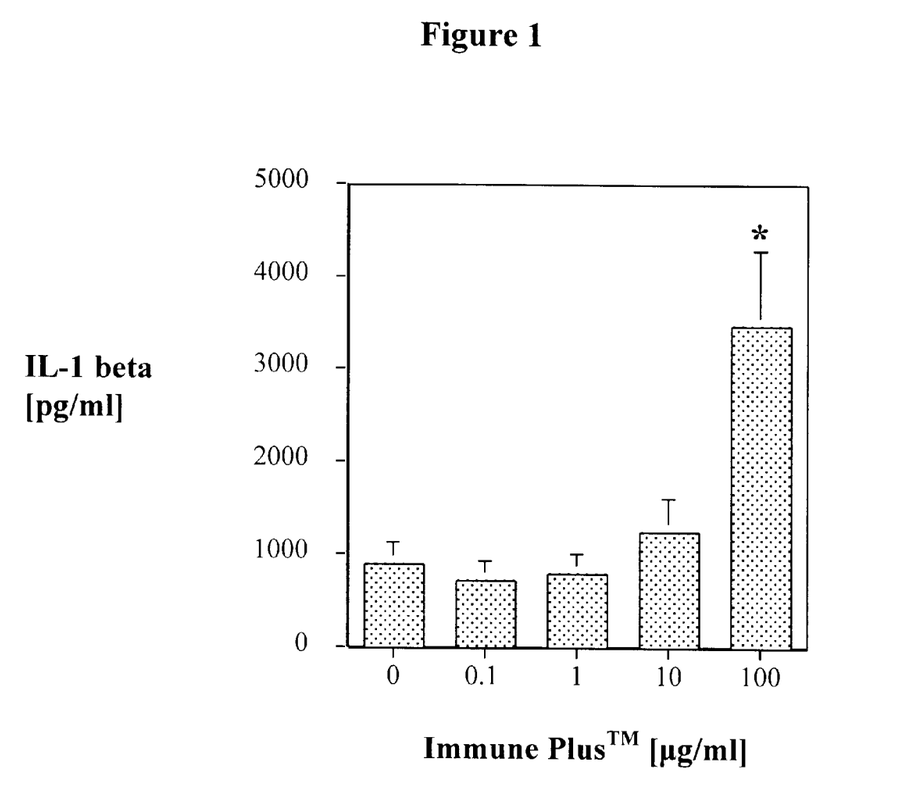
FIG. 1 shows the effect of four different concentrations of Immune+™ on the secretion of IL-1 β following a 72 h incubation with PBMCs. Data are shown as concentration of IL-1 β in pg/ml (mean±sem; n=10). * indicates statistical significance compared to media control, where $p<0.001$.
Figure 2:
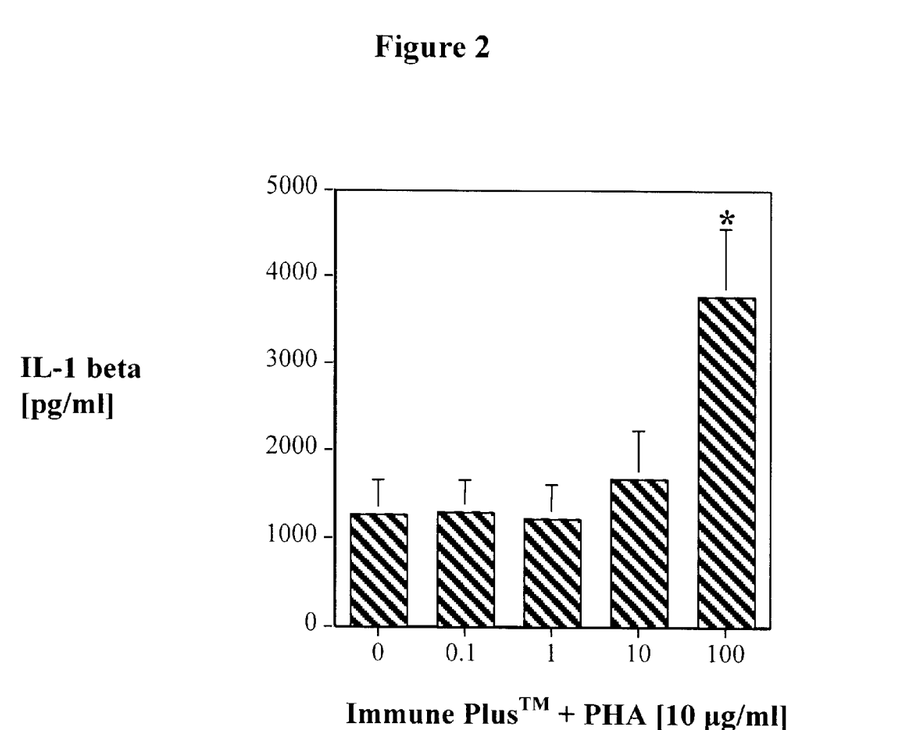
FIG. 2 shows the effect of four different concentrations of Immune+™ combined with 10 μg/ml of PHA on the secretion of IL-1 β following a 72 h incubation with PBMC. Data are shown as concentration of IL-1 β in pg/ml (mean±sem; n=10). * indicates statistical significance compared to PHA control, where $p<0.001$.

The effects of Immune+™ on IL-1β synthesis. In the absence of PHA, a 72-h incubation of PBMC with Immune+™ at 100 μg/ml significantly increased the production of IL-1β from a mean of 900 pg/ml in the media control to a mean of 3460 pg/ml (see FIG. 1). This represented an average change of 317±73% (range: 104–832%, Table 1). No significant changes compared to the media control were observed at any of the lower concentrations (10, 1, and 0.1 μg/ml) of Immune+™, although some individuals did show marked increases. Three subjects, whose cells were exposed to a concentration of 10 μg/ml, displayed a 55–115% increase in IL-1β production. Addition of PHA at 10 μg/ml had little effect on herbal-induced IL-1β synthesis (Table 1). The same concentration of PHA in combination with 100 μg/ml of Immune+™ resulted in a similar increase of IL-1β production as that seen with Immune+™ alone (see FIG. 2). Although the combination of PHA and Immune+™ at 10 μg/ml resulted in higher IL-1β synthesis compared to PHA alone, this increase did not reach statistical significance. The other two concentrations of Immune+™ had no detectable effect on IL-1β synthesis compared to the results obtained with PHA alone.

TABLE 1

The percentage change of IL-1 beta production. PBMCs treated with only Immune+™ were compared to media IL-1 beta levels, while cells co-incubated with PHA (at 10 μg/ml) were compared to PHA control. Data represents mean % change ± SEM (n = 10)

| Group | Dose [μg/ml] | % Change |
|---|---|---|
| Immune+™ only | 0 | — |
|  | 0.1 | −30 ± 6 |
|  | 1 | −22 ± 7 |
|  | 10 | 18 ± 15 |
|  | 100 | 317 ± 73 |
| Immune+™ + PHA | 0 | — |
|  | 0.1 | 11 ± 10 |
|  | 1 | −5.4 ± 5 |
|  | 10 | 27 ± 12 |
|  | 100 | 312 ± 109 |

Figure 3:
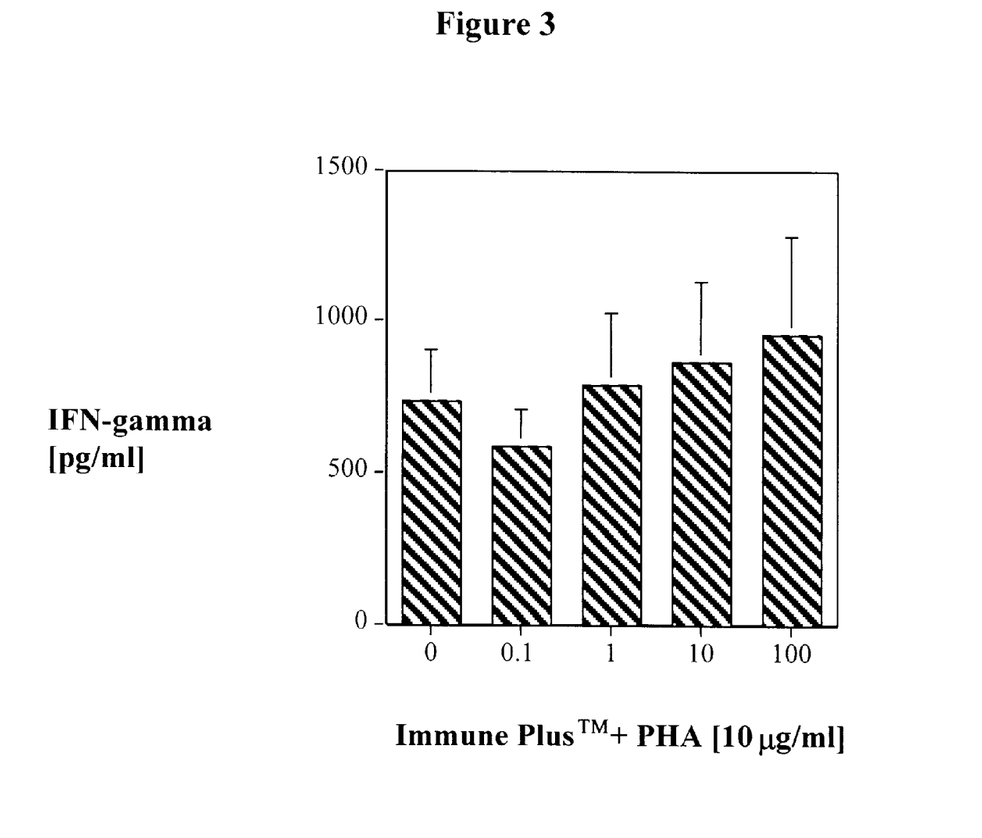
FIG. 3 shows the effect of four different concentrations of Immune+™ co-incubated with 10 μg/ml of PHA on the secretion of IFN-γ following a 72 h incubation with PBMC. Data are shown as concentration of IFN-gamma in pg/ml (mean±sem; n=8).

The effect of Immune+™ on secretion of IFN-γ. In the absence of PHA, little or no IFN-γ was detectable in the supernatant of PBMC cultured for 72 h with either media only (control) or with various concentrations of Immune+™. Thus, under the present experimental conditions, Immune+™ alone did not enhance the synthesis of IFN-γ in PBMC from healthy volunteers. Incubation of PBMC with PHA at a concentration of 10 μg/ml for 72 h resulted in a production of IFN-γ. Immune+™ did not significantly affect the PHA-induced synthesis of IFN-γ at any of the concentrations tested (see FIG. 3, TABLE 2). However, PBMC from two subjects treated at the highest concentration, were able to augment IFN-γ production by 150% of PHA control.

TABLE 2

The percentage change of IFN-gamma production. PBMCs treated with Immune+™ in the presence of PHA (at 10 μg/ml) were compared to PHA control. Data represents mean % change ± SEM (n = 8)

| Group | Dose [μg/ml] | % Change |
|---|---|---|
| Immune+™ + PHA | 0 | — |
|  | 0.1 | −16 ± 11 |
|  | 1 | 4.8 ± 18 |
|  | 10 | 12 ± 19 |
|  | 100 | 24 ± 30 |

Immune+™ is a dietary supplement consisting of the extracts of 5 botanicals frequently used in TCM, namely Radix Glycyrrhizae, Radix Astragali, *Dioscoreae rhizoma*, *Cordyceps sinensis*, and *Hericium erinaceum*. Individually, these botanicals have been shown to exert immunomodulatory effects, but it has not been previously investigated whether and how their combination can influence immune responses. The above reported experiment demonstrated that Immune+™ at 100 μg/ml, significantly increased the secretion of IL-1β by PBMC from healthy volunteers. The combination of Immune+™ with PHA resulted in the same concentrations of IL-1β as those obtained with Immune+™ alone. Little is known about the ability of the other ingredients of Immune+™ to affect IL-1β production. In addition, the extract from a single plant or plant part often exerts different immunomodulatory effects than when it is combined with other plant extracts. It can, therefore, not be determined which ingredient(s) or specific combination of ingredients present in Immune+™ is responsible for the unexpected results in the enhancement of IL-1β production observed. Moreover, Immune+™ did not significantly alter the synthesis of IFN-γ by either unstimulated or PHA-stimulated PBMC.

In a rat model of endometritis, a model in which the production of pro-inflammatory cytokines is increased, a crude extract of Radix Glycyrrhizae given by gavage 3 times daily for 7 days significantly reduced the serum concentrations of IL-1β, as well as TNF-α and IL-6 (Mikamo et al., 1999). In the same study, Radix Glycyrrhizae did not significantly change the serum levels of any of these three cytokines in normal rats. In contrast, in healthy rats treated with *C. sinensis*, a marked dose-dependent increase in IL-1 synthesis by their Kupffer cells was noted (Zhu et al., 1998). Little is known about the ability of the other ingredients of Immune+™ to affect IL-1β production. It is recognized that the extract from a single plant or plant part often exerts different immunomodulatory effects than when it is combined with other plant extracts (Matsuura K et al., 1993, Yamada H et al., 1992). It can, therefore, not be determined which ingredient(s) or specific combination of ingredients present in Immune+™ are responsible for the observed enhancement in IL-1β production.

In this study, Immune+™ alone did not have a detectable effect on IFN-γ production in either unstimulated or stimulated PBMC of healthy volunteers. Glycyrrhizin alone did not markedly alter IFN-γ production of normal PBMC, whereas Con A-stimulated synthesis of this cytokine was 4 to 5-fold greater in PBMC pre-incubated with glycyrrhizin than in those treated only with Con A (Shinada et al., 1986).

The i.p. administration of glycyrrhizin to mice was also found to induce CD4 T cells capable of producing significant amounts of IFN-γ upon stimulation with anti-CD3 antibodies. In addition, Radix Astragali has been reported to upregulate the IFN-γ production of mice whose immune functions were suppressed due to the presence of chemically induced tumors (Kurashige et al., 1999). Based on these data, Immune+™ might have been expected to result in an upregulation of IFN-γ synthesis at least in the presence of PHA. However, it has not been determined whether the crude extract of Radix Glycyrrhizae has the same effect on IFN-γ secretion as glycyrrhizin. It is also not known what effect, if any, the other ingredients of Immune+™ have on IFN-γ production. It is possible that they contain substances that inhibit the IFN-γ inducing activity of glycyrrhizin and Radix Astragli.

The present data allow some extrapolation as to what the in vivo effects of the consumption of Immune+™ might be. If it upregulates IL-1β synthesis in vivo to a similar extent as it does in vitro, it might offer benefit against infectious diseases in which the non-adaptive arm of the immune system plays a vital role.

Licorice root, Radix Glycyrrhizae, is frequently used in Chinese medicinal formulae and has been reported to exert a variety of immunomodulatory effects. Most of the research has focused on glycyrrhizin, one of the major active constituents of Glycyrrhiza spp. It should be noted that, just like botanicals have different bioactivities individually than they do when combined with others, chemicals isolated from a plant frequently exhibit different activities from the crude extract of that plant.

Glycyrrhizin is a saponin used clinically in Japan in the treatment of chronic hepatitis (van Rossum et al., 1998), where its long-term administration appears to protect against the development of hepatocellular carcinoma (Arase et al., 1997). In mice, glycyrrhizin was able to restore a variety of immune responses that were depressed due to thermal injury or murine acquired immunodeficiency syndrome (MAIDS). In both experimental models, intraperitoneal (i.p.) administration of glycyrrhizin provided strong protection against infections with Candida albicans or herpes simplex virus type 1 (Kobayashi et al., 1993, Utsunomiya et al., 2000, Utsunomiya et al., 1995, Utsunomiya et al., 1999).

This protection was at least partly attributable to the induction of CD4 T cells with the ability to shift the cytokine profile from a Th2 type to a Th1 type, i.e., from the production of IL-4 and IL-10 to that of IFN-$\gamma$ and IL-12 (Kobayashi et al., 1995, Nakajima et al., 1996, Utsunomiya et al., 1998, Utsunomiya et al., 1999). Increased IFN-$\gamma$ synthesis has also been reported after in vitro treatment of Concanavalin A (Con A)-stimulated human PBMC with glycyrrhizin (Shinada et al., 1986). In addition, glycyrrizhin accelerated, enhanced, and prolonged the anti-CD3 Ab or Con A-induced IL-2 production and IL-2 receptor (IL-2R) expression of splenic T-lymphocytes obtained from normal mice (Zhang et al., 1993).

In contrast to glycyrrhizin, the crude extract of Radix Glycyrrhizae significantly enhanced the production of IL-10 by PBMC from healthy volunteers (Yamashiki et al., 1997). These and other data (Matsumoto et al., 1996) indicate that biologically active constituents other than glycyrrhizin must be present in Glycyrrhiza root extract.

Radix Astragali is found in numerous Chinese herbal formulae, as it is considered a tonic that can strengthen natural host immune responses. Animal studies have shown that Astragalus can restore a variety of immune functions in situations where the host immune response is depressed due to tumors, cyclophosphamide or radiation treatment, or aging. In particular, macrophage oxidative burst (Rittenhouse et al., 1991), chemotaxis, and cytokine production (Jin et al., 1996), lymphocyte IL-2 and IFN-$\gamma$ production as well as cytotoxic activity (Kurashige et al., 1999), graft versus host (GVH) reaction (Chu et al., 1988, Sun et al., 1983), and T-cell dependent antibody responses (Zhao et al., 1990) were reported to be normalized to the levels seen in immune-competent controls by crude extracts and/or fractions of A. membranaceus.

In vitro, a partially purified fraction of A. membranaceus resulted in a 10-fold potentiation in the ability of low doses of recombinant IL-2 to induce LAK activity (Chu et al., 1988). A. membranaceus also increased mouse spleen cell proliferation, polyclonal Ig production, macrophage tumor necrosis factor (TNF) and IL-6 activity, as well as cytotoxic T cell, but not NK cell, activity in vitro (Yoshida et al., 1997). Others, however, observed a slight, but statistically significant decrease in IL-6 synthesis by mouse splenocytes incubated with A. membranaceus, and reported reduced IgG2a production during the primary, but not the secondary, immune response, while IgG1 was unaffected (Song et al., 2000).

Cordyceps sinensis is another tonic used extensively in TCM preparations for a variety of conditions, including for enhancement of immune responses and the treatment of cancer patients (Zhu et al., 1998, Zhu et al., 1998). This fungus appears to possess immunomodulatory effects particularly on the non-adaptive arm of the immune system. However, the existing data are rather conflicting in that they indicate both immunostimulatory and immunosuppressive activities for C. sinensis (Zhu et al., 1998). For example, an ethanol extract of C. sinensis has been reported to enhance natural killer (NK) cell activity both in vitro and in vivo (Xu et al., 1992), while a water extract was found to activate Kupffer cells in vivo (Nakamura et al., 1999). In contrast, fractions of a methanol extract decreased NK activity and also suppressed IL-2 and TNF-$\alpha$ production (Kuo et al., 1996). These discrepancies may reflect differences in experimental procedures, particularly in the raw material (wild fungus or various cultivated, fermented mycelial products) and the extractions procedures. It is also possible, however, that the conflicting findings indicate that C. sinensis is a true biological response modifier, having different effects on immune functions depending on the host conditions under which it is used. Hericium erinaceum, particularly the polysaccharide fraction of this fungus, has been reported to have anti-tumor activity, thought to be due to its ability to enhance macrophage and NK activity (Mizuno T, 1995).

In the specification, the following references are cited; all are herein incorporated by reference:

Arase, Y., Ikeda, K., Murashima, N., Chayama, K., Tsubota, A., Koida, I., Suzuki, Y., Saitoh, S., Kobayashi, M. and Kumada, H. (1997). The long term efficacy of glycyrrhizin in chronic hepatitis C patients. Cancer 79, 1494–1500.

Boehm, U., Klamp, T., Groot, M. and Howard, J. (1997). Cellular responses to interferon-$\gamma$. Annu Rev Immunol 15, 749–795.

Cassidy, C. M. (1998). Chinese medicine users in the United States part I: utilization, satisfaction, medical plurality. J. Alt. Comp. Med. 4, 17–27.

Cassidy, C. M. (1998). Chinese medicine users in the United States part II: preferred aspects of care. J. Alt. Comp. Med. 4, 189–202.

Chu, D. T., Lepe-Zuniga, J., Wong, W. L., LaPushin, R. and Mavligit, G. M. (1988). Fractionated extract of Astragalus membranaceus, a Chinese medicinal herb, potentiates LAK cell cytotoxicity generated by a low dose of recombinant interleukin-2. J Clin Lab Immunol 26, 183–187.

Chu, D. T., Wong, W. L. and Mavligit, G. M. (1988). Immunotherapy with Chinese medicinal herbs. II. Reversal of cyclophosphamide-induced immune suppression by administration of fractionated Astragalus membranaceus in vivo. J Clin Lab Immunol 25, 125–129.

Eisenberg, D. M., Davis, R. B., Ettner, S. L., Appel, S., Wilkey, S., Van Rompay, M. and Kessler, R. C. (1998). Trends in alternative medicine use in the United States, 1990–1997: results of a follow-up national survey. JAMA, J. Am. Med. Assoc. 280, 1569–1575.

Eisenberg, D. M., Kessler, R. C., Foster, C., Norlock, F. E., Calkins, D. R. and Delbanco, T. L. (1993). Unconventional medicine in the United States: prevalence, costs, and patterns of use. N. Engl. J. Med. 328, 246–252.

Jin, R. and Kurashige, S. (1996). Effects of Chinese herbs on macrophage functions in N-butyl-N-butanolnitrosoamine treated mice. Immunopharmacol Immunotoxicol 18, 105–114.

Kobayashi, M., Herndon, D. N., Pollard, R. B. and Suzuki, F. (1995). CD4+ contrasuppressor T cells improve the resistance of thermally injured mice infected with HSV. *J Leukoc Biol* 58, 159–167.

Kobayashi, M., Schmitt, D. A., Utsunomiya, T., Pollard, R. B. and Suzuki, F. (1993). Inhibition of burn-associated suppressor cell generation by glycyrrhizin through the induction of contrasuppressor T cells. *Immunol Cell Biol* 71, 181–189.

Kuo, Y. C., Tsai, W. J., Shiao, M. S., Chen, C. F. and Lin, C. Y. (1996). Cordyceps sinensis as an immunomodulatory agent. *Am J Chin Med* 24, 111–125.

Kurashige, S., Akuzawa, Y. and Endo, F. (1999). Effects of astragali radix extract on carcinogenesis, cytokine production, and cytotoxicity in mice treated with a carcinogen, N-butyl-N'-butanolnitrosoamine. *Cancer Invest* 17, 30–35.

MacLennan, A. H., Wilson, D. H. and Taylor, A. W. (1996). Prevalence and cost of alternative medicine in Australia. *Lancet* 347, 569–573.

Matsunoto, T., Tanaka, M., Yamada, H. and Cyong, J.-C. (1996). Effect of licorice roots on carrageenan-induced decrease in immune complexes clearance in mice. *J Ethnopharmacol* 53, 1–4.

Matsuura K, Kawakita T, Nakai S, Saito Y, Suzuki A and Nomoto K. (1993). Role of B-lymphocytes in the immunopharmacological effects of a traditional Chinese medicine, Xiao-Chai-Hu-Tang (Shosaiko-to). *Int. J. Immunopharmacol.* 15, 237–243.

Mikamo, H., Kawazoe, K., Sato, Y., Hayasaki, Y., Izumi, K. and Tamaya, T. (1999). Effects of crude herbal ingredients on serum levels of inflammatory cytokines in a rat uterine endometritis model. *Curr Ther Res* 60, 105–110.

Mizuno T. (1995). Yamagushitake, *Hericium erinaceum*: Bioactive substances and medicinal utilization. *Food Rev Int* 11, 173–178.

Nakajima, N., Utsunomiya, T., Kobayashi, M., Herndon, D. N., Pollard, R. B. and Suzuki, F. (1996). In vitro induction of anti-type 2 T cells by glycyrrhizin. *Burns* 22, 612–617.

Nakamura, K., Yamaguchi, Y., Kagota, S., Shinozuka, K. and Kunitomo, M. (1999). Activation of in vivo Kupffer cell function by oral administration of *Cordyceps sinensis* in rats. *Jpn J Pharmacol* 79, 505–508.

Rittenhouse, J. R., Lui, P. D. and Lau, B. H. S. (1991). Chinese medicinal herbs reverse macrophage suppression induced by urological tumors. *J Urol* 146, 486–490.

Shinada, M., Azuma, M., Kawai, H., Sazaki, K., Yoshida, I., Yoshida, T., Suzutani, T. and Sakuma, T. (1986). Enhancement of interferon-gamma production in glycyrrhizin-treated human peripheral lymphocytes in response to concavalin A and to surface antigen of hepatitis B virus. *Proc Soc Exp Biol Med* 181, 205–210.

Song, Q.-H., Kobayashi, T., Xiu, L.-M., Hong, T. and Cyong, J.-C. (2000). Effects of Astragali root and Hedysari root on the murine B and T cell differentiation. *J Ethnopharmacol* 73, 111–119.

Sun, Y., Hersh, E. M., Talpaz, M., Lee, S., Wong, W., Loo, T. L. and Mavligit, G. M. (1983). Immune restoration and/or augmentation of local graft versus host reaction by traditional Chinese medicinal herbs. *Cancer Invest* 52, 70–73.

Tomlinson, B., Chan, T. Y. K., Chan, J. C. N., Critchley, J. A. J. H. and But, P. P. H. (2000). Toxicity of complementary therapies: An eastern perspective. *Journal of Clinical Pharmacology* 40, 451–456.

Utsunomiya, T., Ito, M., Pollard, R. B. and Suzuki, F. (2000). Glycyrrhizin improves the resistance of MAIDS mice to opportunistic infection of *Candida albicans* through the modulation of MAIDS-associated type 2 T cell responses. *Clin Immunol* 95, 145–155.

Utsunomiya, T., Kobayashi, M., Herndon, D. N., Pollard, R. B. and Suzuki, F. (1995). Glycyrrhizin (20β-carboxy-11-oxo-30-norolean-12-en-3 βyl-2-O-β-D-glucopyranuronosyl-α-D-glucopyranosiduronic acid) improves the resistance of thermally injured mice to opportunistic infection of herpes simplex virus type 1. *Immuno Lett* 44, 59–66.

Utsunomiya, T., Kobayashi, M., Herndon, D. N., Pollard, R. B. and Suzuki, F. (1998). Recovery of impaired IL-12 production in thermally injured mice treated with glycyrrhizin (GR), and active component of licorice roots. *FASEB J* 12, A27 1.

Utsunomiya, T., Kobayashi, M., Herndon, D. N., Pollard, R. B. and Suzuki, F. (1999). Effects of glycyrrhizin, an active component of licorice roots, on *Candida albicans* infection in thermally injured mice. *Clin Exp Immunol* 116, 291–298.

Utsunomiya, T., Kobayashi, M., Pollard, R. B. and Suzuki, F. (1999). Restoration of the impaired production of IL-12 in MAIDS mice treated with glycyrrhizin. *Am Soc Microbiol Abstr General Meeting* 99, 289.

van Rossum, T., Vulto, A., de Man, R., Brouwer, J. and Schalm, S. (1998). Review article: glycyrrhizin as a potential treatment for chronic hepatitis C. *Aliment Pharmacol Ther* 12, 199–205.

Xu, R. H., Peng, X. E., Chen, G. Z. and Chen, G. L. (1992). Effects of cordyceps sinensis on natural killer activity and colony formation of B 16 melanoma. *Chin Med J (Engl).* 105, 97–101.

Yamada H, Kiyohara H, Takemoto N, Zhao J-F, Kawamura H, Komatsu Y, Cyong J-C, Aburada M and Hosoya E. (1992). Mitogenic and complement activating activities of the herbal components of Juzen-taiho-to. *Planta Med.* 58, 166–170.

Yamashiki, M., Nishimura, A., Suzuki, H., Sakaguchi, S. and Kosaka, Y. (1997). Effects of the Japanese herbal medicine "Sho-saiko-to" (TJ-9) on in vitro interleukin-10 production by peripheral blood mononuclear cells of patients with chronic hepatitis C. *Hepatology* 25, 1390–1397.

Yoshida, Y., Wang, M. Q., Liu, J. N., Shan, B. E. and Yamashita, U. (1997). Immunomodulating activity of Chinese medicinal herbs and *Oldenlandia diffusa* in particular. *Int J Immunopharmacol* 19, 359–370.

Zhang, Y. H., Isobe, K., Nagase, F., Lwin, T., Kato, M., Hamaguchi, M. and Yokochi, T. (1993). Glycyrrhizin as a promoter of the late signal transduction for interleukin-2 production by splenic lymphocytes. *Immunology* 79, 528–534.

Zhao, K. S., Mancini, C. and Doria, G. (1990). Enhancement of the immune response in mice by *Astragalus membranaceus* extracts. *Immunopharmacology* 20, 225–233.

Zhu, J.-S., Halpern, G. M. and Jones, K. (1998). The scientific rediscovery of an ancient Chinese herbal medicine: *Cordyceps sinensis*. Part I. *J Altern Complement Med* 4, 289–303.

Zhu, J.-S., Halpern, G. M. and Jones, K. (1998). The scientific rediscovery of an ancient Chinese herbal medicine: *Cordyceps sinensis*. Part II. *J Altern Complement Med* 4, 429–457.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A pharmaceutical composition comprising an immune system stimulator composition, said immune system stimulator composition comprising herbs, or extracts thereof, of: Hericium, *Radix Astragali, Cordyceps Sinensus, Radix Glycyrrhizae* and *Dioscoreae Oppositae*; wherein said immune system stimulator composition is present at a concentration effective for providing immune system stimulation to a human or other mammal.

2. The immune system stimulator of claim 1, wherein said herbs or extracts thereof of said immune system stimulator composition comprise 5–80% by weight Hericium, 5–40% by weight *Radix Astragali,* 5–40% by weight *Cordyceps Sinensus,* 1–40% by weight *Radix Glycyrrhizae* and 5–40% by weight *Dioscoreae Oppositae.*

3. The immune system stimulator of claim 1, wherein said herbs or extracts thereof of said immune system stimulator composition comprise 40–70% by weight Hericium, 10–50% by weight *Radix Astragali,* 5–30% by weight *Cordyceps Sinensus,* 1–30% by weight *Radix Glycyrrhizae* and 5–30% by weight *Dioscoreae Oppositae.*

4. The immune system stimulator composition of any of claims 1, 2 or 3, wherein said herbs or extracts thereof are powdered.

5. The immune system stimulator composition of claim 4, wherein said said herbs or extracts thereof are incorporated into a pill.

6. The immune system stimulator composition of claim 4, wherein said said herbs or extracts thereof are incorporated into a capsule.

7. The immune system stimulator composition of claim 4, wherein said said herbs or extracts thereof are incorporated into a gel cap.

8. The immune system stimulator composition of claim 1, wherein said herbs or extracts thereof are powdered and incorporated into a pill, capsule, or gel cap.

9. The immune system stimulator composition of claim 8, wherein said concentration effective for providing immune system stimulation is 100 mg per dose.

10. The immune system stimulator composition of claim 2, wherein said herbs or extracts thereof are powdered and incorporated into a pill, capsule, or gel cap.

11. The immune system stimulator composition of claim 10, wherein said concentration effective for providing immune system stimulation is 100 mg per dose.

12. The immune system stimulator composition of claim 3, wherein said herbs or extracts thereof are powdered and incorporated into a pill, capsule, or gel cap.

13. The immune system stimulator of claim 12, wherein said concentration effective for providing immune system stimulation is 100 mg per dose.

14. A method of making a pharmaceutical composition comprising an immune system stimulator composition, said immune system stimulator composition comprising herbs, or extracts thereof, of: Hericium, *Radix Astragali, Cordyceps Sinensus, Radix Glycyrrhizae,* and *Dioscoreae Oppositae*; said method comprising the steps of:

(a) obtaining powdered Hericium, *Radix Astragali, Cordyceps Sinensus, Radix Glycyrrhizae,* and *Dioscoreae Oppositae;* and (b) mixing 5–80% by weight Hericium, 5–40% by weight *Radix Astragali,* 5–40% by weight *Cordyceps Sinensus,* 1–40% by weight *Radix Glycyrrhizae* and 5–40% by weight *Dioscoreae Oppositae* together.

15. The method of claim 14, wherein the mixture formed in said step (b) comprises 40–70% by weight Hericium, 10–50% by weight *Radix Astragali,* 5–30% by weight *Cordyceps Sinensus,* 1–30% by weight *Radix Glycyrrhizae* and 5–30% by weight *Dioscoreae Oppositae.*

16. The method of any of claim 14 or 15, wherein method further comprises formulating said mixture into a pill.

17. The method of claim 16, wherein said pill contains 100 mg of said mixture.

18. The method of any of claim 14 or 15, wherein method further comprises formulating said mixture into a capsule.

19. The method of claim 18, wherein said capsule contains 100 mg of said mixture.

20. The method of any of claim 14 or 15, wherein method further comprises formulating said mixture into a gel cap.

21. The method of claim 20, wherein said gel cap contains 100 mg of said mixture.

22. A method of stimulating the immune system of a human or other mammal comprising providing to said human or other mammal a biologically effective amount of a pharmaceutical composition comprising an immune system stimulator composition, said immune system stimulator composition comprising herbs, or extracts thereof, of: Hericium, *Radix Astragali, Cordyceps Sinensus, Radix Glycyrrhizae* and *Dioscoreae Oppositae, wherein said immune system stimulator composition is provided at a concentration effective for providing immune system stimulation to a human or other mammal.*

23. The method of stimulating the immune system of a human or other mammal of claim 22, wherein said herbs or extracts thereof of said immune system stimulator composition comprise 5–80% by weight Hericium, 5–40% by weight *Radix Astragali,* 5–40% by weight *Cordyceps Sinensus,* 1–40% by weight *Radix Glycyrrhizae* and 5–40% by weight *Dioscoreae Oppositae.*

24. The method of stimulating the immune system of a human or other mammal of claim 23, wherein said herbs or extracts thereof of said immune system stimulator comprise 40–70% by weight Hericium, 10–50% by weight *Radix Astragali,* 5–30% by weight *Cordyceps Sinensus,* 1–30% by weight *Radix Glycyrrhizae* and 5–30% by weight *Dioscoreae Oppositae.*

25. The method of stimulating the immune system of a human or other mammal of any of claims 22–24, wherein said concentration effective for providing immune system stimulation is 100 mg per dose.

* * * * *